United States Patent [19]

Ohsumi et al.

[11] Patent Number: 5,049,575
[45] Date of Patent: * Sep. 17, 1991

[54] SUBSTITUTED CARBOXYLIC ACID, FUNGICIDAL COMPOSITIONS AND USE

[75] Inventors: Tadashi Ohsumi, Nishinomiya; Tatsuya Mori, Toyonaka; Sumio Nishida, Tokyo; Shigeo Nakamura, Sendai; Kiyoto Maeda, Nishinomiya; Hirotaka Takano, Sanda, all of Japan

[73] Assignee: Sumitomo Chemical Company, Osaka, Japan

[*] Notice: The portion of the term of this patent subsequent to Oct. 31, 2006 has been disclaimed.

[21] Appl. No.: 431,668

[22] Filed: Nov. 3, 1989

[30] Foreign Application Priority Data

Nov. 10, 1988 [JP] Japan ............................. 63-285304
Dec. 2, 1988 [JP] Japan ............................. 63-306665

[51] Int. Cl.$^5$ .................... A01N 43/56; C07D 405/12
[52] U.S. Cl. .................................. 514/406; 548/374; 549/462; 549/469
[58] Field of Search ................... 548/374; 514/406

[56] References Cited

U.S. PATENT DOCUMENTS 4,742,074  5/1988  Nishida et al. .
4,837,242  6/1989  Ohsumi et al. .
4,877,441 10/1989  Mori et al. .......................... 548/374

Primary Examiner—Robert W. Ramsuer
Attorney, Agent, or Firm—Ladas & Parry

[57] ABSTRACT

Fungicide contains a substituted pyrazole carboxylic acid of the formula:

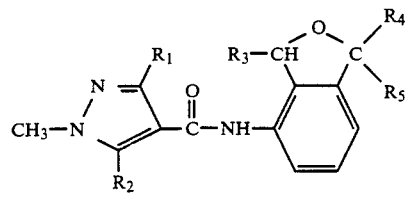

wherein $R_1$ is a methyl or trifluoromethyl group, $R_2$ is halogen atom, $R_3$ and $R_4$ are, same or different, a methyl or ethyl and $R_5$ is an ethyl, propyl, butyl group or hydrogen atom.

7 Claims, No Drawings

SUBSTITUTED CARBOXYLIC ACID, FUNGICIDAL COMPOSITIONS AND USE

The present invention relates to substituted carboxylic acid derivatives (hereinafter referred to as the present compound) having the formula:

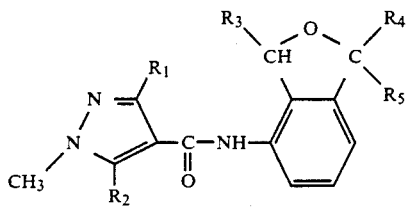 (I)

wherein $R_1$ is a methyl or trifluoromethyl group; $R_2$ is a halogen atom; $R_3$ and $R_4$ are, same or different, a methyl or ethyl group; $R_5$ is an ethyl, propyl, butyl group or hydrogen atom.

The halogen atoms are, for example, a fluorine, chlorine, bromine and iodine atom.

According to the present invention, processes for preparing the present compound and agricultural or horticultural fungicides containing the present compound as an active ingredient are provided, too.

Fungicidal activity of some carboxylic acid derivatives is reported in e.g., Japanese Patent Kokai Nos. 52-87168 (U.S. Pat. No. 4,134,987) and 60-34949. However, chemicals have been demanded which have higher fungicidal activity, since those known compounds are not satisfactory in activity After extensive research on compounds having high fungicidal activity, the present inventors have found substituted carboxylic acid derivatives having the formula (I).

Among the substituted carboxylic acid derivatives having the formula (I), preferred are those wherein $R_1$ is a methyl or trifluoromethyl group; $R_2$ is a chlorine atom; $R_3$ and $R_4$ are, same or different, a methyl or ethyl group; $R_5$ is an ethyl, n-propyl, n-butyl group or hydrogen atom.

The present compound has preventive, curative and systemic controlling effects on various plant microbes, especially on plant diseases caused by microbes belonging to Basidiomycetes and gives almost no adverse influence to environment.

The following are plant diseases on which the present compound has an excellent controlling effect; *Rhizoctonia solani* and *Rhizoctonia oryzae*, *R. solani* IIIB on rice plant; *Puccinia striiformis*, *P. graminis*, *P. recondita*, *P. hordei*, *Typhula incarnata*, *T. ishikariensis*, *Ustilago tritici* and *U. nuda* on wheat and barley; *Rhizoctonia solani* and *Corticium rolfsii* on various crops; *Rhizoctonia solani* on potato and beet; *Gymnosporangium haraeanum* on pear; *Venturia inaequalis* on apple; *Rhizoctonia solani*, *Corticium rolfsii*, *Uromyces trifolii* and *Typhula incarnata*, *T. ishikariensis* on pasture and lawn.

Method for preparing the present compound will be explained in detail below.

[Method (A)]

The present compound, a substituted carboxylic acid derivative having the formula:

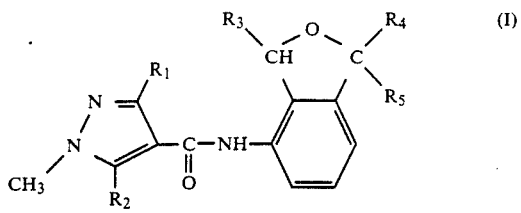

wherein $R_1$ and $R_2$ are each as defined above, is prepared by allowing a pyrazole carboxylic acid having the formula:

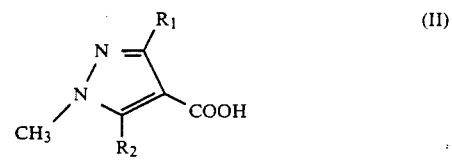

wherein $R_1$ and $R_2$ are each as defined above, or its reactive derivative to react with a substituted 4-amino-2-oxaindan derivative having the formula:

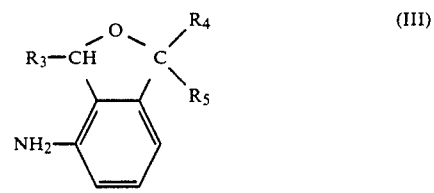

wherein $R_3$, $R_4$ and $R_5$ are each as defined above.

The reaction is usually conducted in the presence of solvent which is not always necessary. The solvents are, for example, hydrocarbons such as benzene, toluene and xylene, halogenated hydrocarbons such as chlorobenzene, methylene chloride, chloroform and carbon tetrachloride, ethers such as diisopropyl ether, tetrahydrofuran and dioxane, ketones such as acetone and methyl ethyl ketone, esters such as ethyl acetate, nitriles such as acetonitrile, dimethylsulfoxide, dimethylformamide, water, etc., preferably tetrahydrofuran.

Amounts of the reagents used in said reaction are 0.4-1.5 equivalents, preferably 0.5-1.1 equivalents of the substituted pyrazole carboxylic acid represented by the formula (II) or its reactive derivative thereof per equivalent of the substituted 4-amino-2-oxaindan derivative represented by the formula (III).

The reaction is carried out at optional temperature from the freezing point to the boiling point of the solvent, preferably from 0° C. to the boiling point of the solvent.

The reaction is usually carried out for 0.5-20 hours.

The substituted pyrazole carboxylic acid represented by the formula (II) or its reactive derivative thereof includes the corresponding carboxylic acids, acid anhydrides, acid chlorides, acid bromides, carboxylic esters, etc.

The reaction may be conducted in the presence of a reaction assistant depending on the substituted pyrazole carboxylic acids represented by the formula (II) or its reactive derivatives thereof. The reaction assistant is, for example, 1-(3-dimethylaminopropyl)-3-ethylcarbodiimidemethiodide and dicyclohexylcarbodiimide when carboxylic acid is used, sodium hydride, sodium methylate, sodium ethylate, etc. when carboxylic ester is used, and sodium hydroxide, potassium hydroxide, triethylamine, N-methylmorpholine, pyridine etc., when acid halide or acid anhydride is used. The reaction assistant is usually used in an amount of less than 2 equivalents, preferably 0.95-1.1 equivalents per equivalent of the substituted pyrazole carboxylic acid represented by the formula (II) or its reactive derivative.

After the reaction is over, the reaction assistant or reaction products thereof are removed by filtration or washing with water. The solvent is removed by distillation to give the desired substituted pyrazole carboxylic acid derivatives of the formula (I). If necessary, the product is further subjected to chromatography, recrystallization, etc. in order to purify the same.

Some of representative compounds of the present invention which are able to be produced by these methods are shown in Table 1.

TABLE 1

Compound represented by the formula:

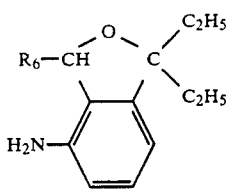

| Compound No. | $R_1$ | $R_2$ | $R_3$ | $R_4$ | $R_5$ |
|---|---|---|---|---|---|
| (1) | $CH_3$ | Cl | $CH_3$ | $CH_3$ | H |
| (2) | $CH_3$ | Cl | $CH_3$ | $CH_3$ | $C_2H_5$ |
| (3) | $CH_3$ | Cl | $CH_3$ | $CH_3$ | n-$C_3H_7$ |
| (4) | $CH_3$ | Cl | $CH_3$ | $CH_3$ | n-$C_4H_9$ |
| (5) | $CH_3$ | F | $CH_3$ | $CH_3$ | n-$C_3H_7$ |
| (6) | $CH_3$ | Cl | $CH_3$ | $C_2H_5$ | H |
| (7) | $CH_3$ | Cl | $CH_3$ | $C_2H_5$ | $C_2H_5$ |
| (8) | $CH_3$ | Cl | $C_2H_5$ | $CH_3$ | $C_2H_5$ |
| (9) | $CF_3$ | Cl | $CH_3$ | $CH_3$ | n-$C_3H_7$ |

[Method (B)]

Substituted 4-amino-2-oxaindan derivative having the formula (IV):

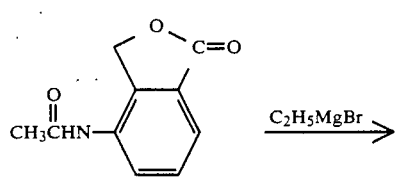

where $R_6$ stands for a methyl or ethyl group, one of the starting materials having the formula (III) for preparing the present compound, is prepared, for example, from 4-acetaminophthalide mentioned in Jean Vene and Jean Tirouflet, Comput rend 231, 911-12 (1950):

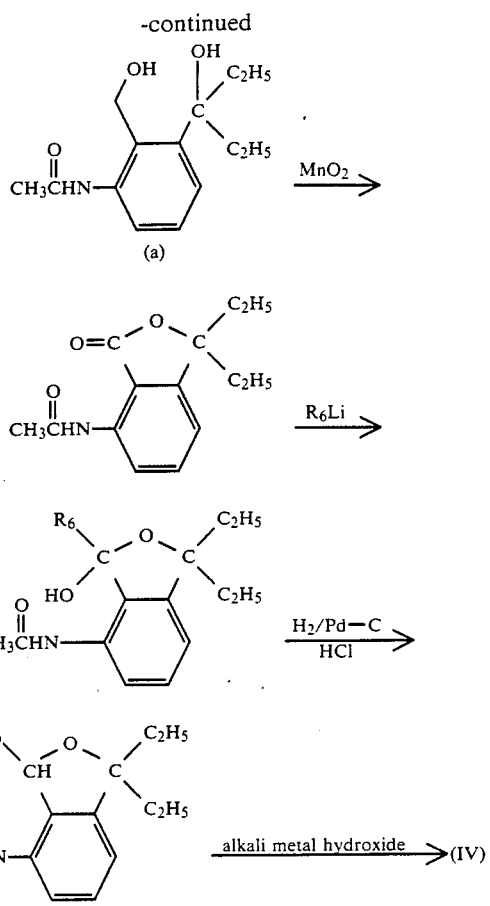

wherein $R_6$ is as defined above

That is, 4-acetaminophthalide is allowed to react with an ethyl Grignard reagent such as ethylmagnesium bromide (4-12 equivalents) in an ether solvent such as diethyl ether and tetrahydrofuran at a temperature from −10° C. to room temperature, until diol (a) is obtained The diol (a) is allowed to react with activated manganese dioxide (5-20 equivalents) in an ether solvent such as dioxane and tetrahydrofuran or a halogenated hydrocarbon solvent such as chloroform and dichloroethane under refluxing to obtain lactone (b). Then, the lactone (b) is allowed to react with methyllithium or ethyllithium (2-4 equivalents) in an ether solvent such as diethyl ether and tetrahydrofuran at a temperature from −30° C. to room temperature until acetal (c) is obtained. The acetal (c) is allowed to react with hydrogen in an alcohol solvent such as methanol and ethanol at room temperature in the presence of catalytic amounts of palladium carbon and hydrochloric acid until anilide (d) is obtained. The anilide (d) is then allowed to react with alkali metal hydroxide such as sodium hydroxide and potassium hydroxide (5-20 equivalents) in an ethylene glycol and water solvent under refluxing, until substituted 4-amino-2-oxaindan derivative (IV) is obtained.

[Method (C)]

Substituted 4-amino-2-oxaindan derivative having the formula (V):

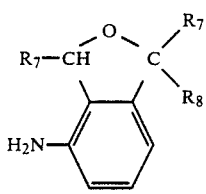
(V)

wherein $R_7$ is a methyl or ethyl group; $R_8$ is an ethyl, propyl, butyl group, is prepared, for example, from 3-acetaminophthalide anhydride mentioned in Yuki gousei kagaku, 26, 685 (1968):

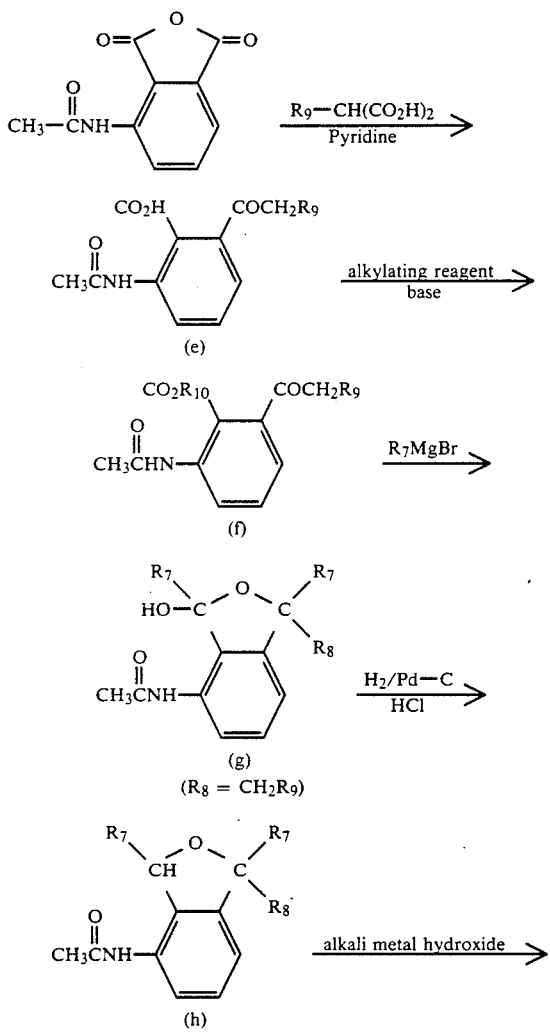

wherein $R_7$ and $R_8$ are each as defined above; $R_9$ is a methyl, ethyl or propyl group; $R_{10}$ is a lower alkyl ($C_1$-$C_3$) group.

That is, 3-acetaminophthalide anhydride to react with malonic acid or α-alkyl $C_1$-$C_3$) malonic acid (1-5 equivalents) in pyridine under heating, until carboxylic acid (e) is obtained. The carboxylic acid (e) is allowed to react with an alkylating reagent such as alkyl halide and dialkyl sulfate (1-2 equivalents) in the presence of a base such as potassium carbonate (1-2 equivalents) under heating until ester (f) is obtained. The ester (f) is allowed to react with methylmagnesium bromide or ethylmagnesium bromide (4-10 equivalents) in an ether solvent such as diethyl ether and tetrahydrofuran at a temperature from $-10°$ C. to $10°$ C. until acetal (g) is obtained. The acetal (g) is allowed to react with hydrogen in an alcohol solvent such as methanol and ethanol at room temperature in the presence of catalytic amounts of palladium carbon and hydrochloric acid until anilide (h) is obtained. The anilide (h) is then allowed to react with alkali metal hydroxide such as sodium hydroxide and potassium hydroxide (5-20 equivalents) in an ethylene glycol and water solvent under refluxing, until its substituted 4-amino-2-oxaindan derivative (V) is obtained.

[Method (D)]

Substituted 4-amino-2-oxaindan derivative having the formula (VI):

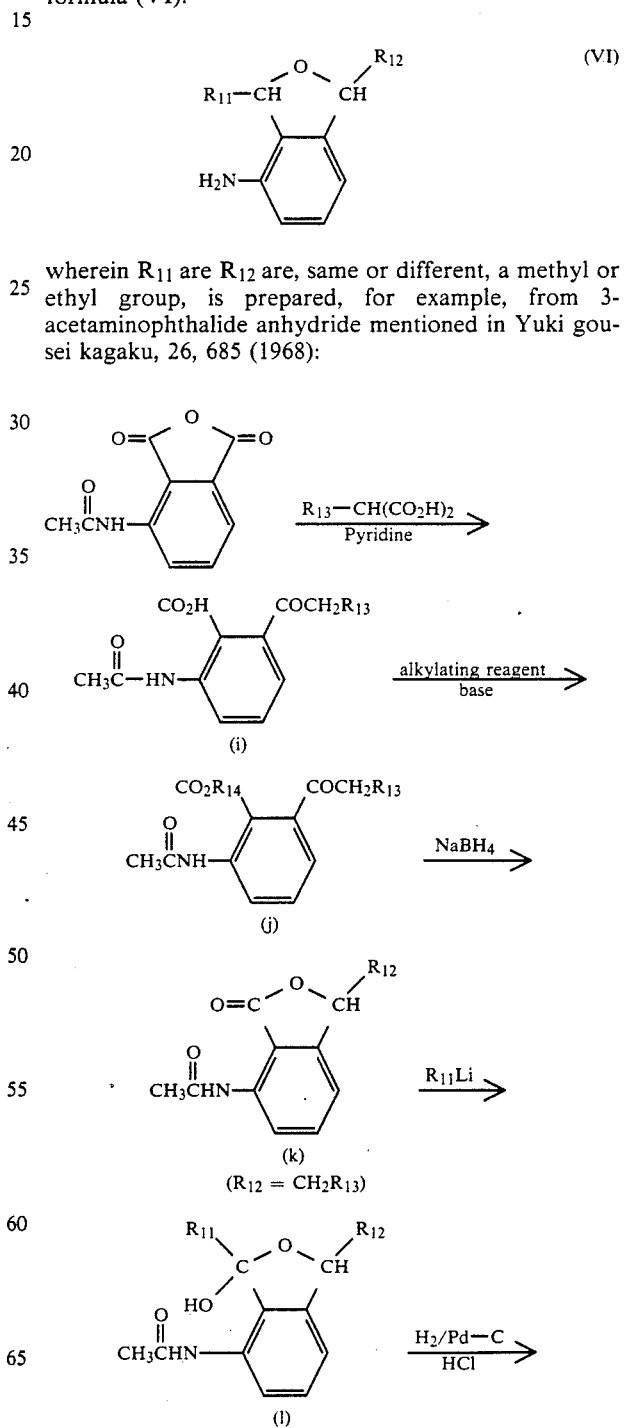

wherein $R_{11}$ are $R_{12}$ are, same or different, a methyl or ethyl group, is prepared, for example, from 3-acetaminophthalide anhydride mentioned in Yuki gousei kagaku, 26, 685 (1968):

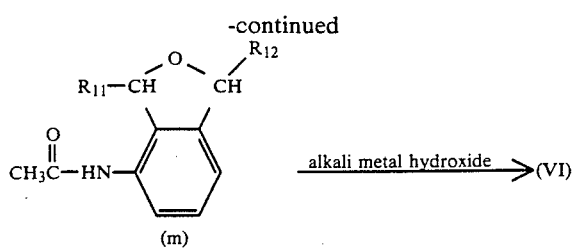

wherein $R_{11}$ and $R_{12}$ are each as defined above; $R_{13}$ is a methyl group or hydrogen atom; $R_{14}$ is a lower alkyl group ($C_1$-$C_3$).

That is, 3-acetaminophthalide anhydride is allowed to react with malonic acid or α-alkyl ($C_1$-$C_3$) malonic acid (1-5 equivalents) in pyridine under heating, until carboxylic acid (i) is obtained. The carboxylic acid (i) is allowed to react with an alkylating reagent such as alkyl halide and dialkyl sulfate (1-2 equivalents) in the presence of a base such as potassium carbonate (1-2 equivalents) under heating until ester (j) is obtained. The ester (j) is allowed to react with sodium brohydride (1-4 equivalents) in an aqueous alcohol at a temperature from 0° C. to room temperature until lactone (k) is obtained. The lactone (k) is then allowed to react with methyllithium or ethyllithium (2-4 equivalents) in an ether solvent such as diethyl ether and tetrahydrofuran at a temperature from −30° C. to room temperature until acetal (l) is obtained. The acetal (l) is allowed to react with hydrogen in an alcohol solvent such as methanol and ethanol at room temperature in the presence of catalytic amounts of palladium carbon and hydrochloric acid until anilide (m) is obtained. The anilide (m) is then allowed to react with alkali metal hydroxide such as sodium hydroxide and potassium hydroxide (5-20 equivalents) in an ethylene glycol and water solvent under refluxing, until substituted 4-amino-2-oxaindan derivative (VI) is obtained.

When the present compound is used as an active ingredient of fungicides, it may be used without adding any other components, but usually, it is formulated into emulsifiable concentrates, wettable powders, suspension formulations, granules, dusts, liquids and the like by mixing with a solid or liquid carrier, a surface active agent and other auxiliaries for formulation.

The content of the present compound as an active ingredient in these formulations is 0.1 to 99.9%, preferably 0.2 to 80% by weight.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. The liquid carrier includes, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water and the like.

The surface active agents used for emulsificaton, dispersion, wetting, etc. include, for example, anionic surface active agents such as salts of alkyl sulfate, alkyl or aryl sulfonates, dialkyl-sulfosuccinates, salt of polyoxyethylene alkylaryl ether phosphoric acid esters, naphtalene-sulfonic acid/formalin condensates, etc. and nonionic surfate active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include, for example, lignosulfonates, alginates, polyvinyl alcohol, gum arabic, CMC (carboxymethyl cellulose), PAP (acid isopropyl phosphate), etc.

These formulations as such or diluted with, for example, water are applied to soil or directly to plants and used for submerged application, too. In more detail, they are use in various forms, e.g., spraying or dusting on plants or spraying, dusting or granule-sprinkling onto soil surface, paddy field surface or if necessary, subsequent further soil incorporation. Furthermore, when they are used as seed treating agents, seeds are covered therewith or dipped therein. These formulations may also be used in admixture with other fungicides, insecticides, acaricides, nematocides, herbicides, plant growth regulating agents, fertilizers, soil improvers and the like.

The present compounds are used as an active ingredient of fungicides to be used for patty field, plowland, orchard, tea garden, pasture, turf and the like.

When the present compound is used as an active ingredient of fungicide, its dosage is usually 0.5 to 100 g, preferably 1 to 50 g per are, although it depends on weather conditions, form of formulations, time, method and place of application, diseases to be controlled, crops to be treated, etc. When the emulsification concentrate, wettable powder, suspension formulation, liquid formulation, etc. are diluted with water for use, the concentration is 0.0001% to 1%, preferably 0.0005% to 0.5%. Granule and dust are used as they are without any dilution.

The present compound is able to be used as an active ingredient of fungicides for various kinds of applications, since the present compound is remarkably active against various plant diseases, particularly those by microorganisms belonging to Basidiomycetes.

The present invention will be explained in more detail by the following synthesis examples, reference examples, formulation examples and text example. And besides, the present invention is not limited of the above examples.

Synthesis Example 1

[Synthesis of compound (3) by method (A)]

To a solution of 80 mg of 1,3-dimethyl-1-n-propyl-2-oxa-4-aminoindan and 48 mg of triethylamine in 5 ml of tetrahydrofuran was added dropwise with stirring below 5° C. of inner temperature under ice cooling, a solution of 76 mg of 5-chloro-1,3-dimethyl pyrazole-4-carbonyl chloride in 2 ml of tetrahydrofuran, followed by stirring at room temperature overnight. The reaction mixture was extracted with water and chloroform. The organic layer was washed with water, dried and concentrated. The residue was purified by silica gel thin layer chromatography to obtain 121 mg of N-(1,3-dimethyl-1-n-propyl-2-oxa-4-indanyl)-5-chloro-1,3-dimethyl pyrazole-4-carboxamide.

Some of representative compounds of the present invention which were produced by these methods are shown in Table 2.

TABLE 2

Compound represented by the formula:

[Structural formula shown with substituents R1, R2, R3, R4, R5, CH3, N, O, CNH groups]

| Compound No. | R1 | R2 | R3 | R4 | R5 | Melting point (°C.) |
|---|---|---|---|---|---|---|
| (1) | CH3 | Cl | CH3 | CH3 | H | 188.6 |
| (2) | CH3 | Cl | CH3 | CH3 | C2H5 | 132.9 |
| (3) | CH3 | Cl | CH3 | CH3 | n-C3H7 | 123.8 |
| (6) | CH3 | Cl | CH3 | C2H5 | H | 181.8 |
| (7) | CH3 | Cl | CH3 | C2H5 | C2H5 | 60.5 |
| (8) | CH3 | Cl | C2H5 | CH3 | C2H5 | 87.2 |

Synthesis Example 2

Synthesis of α,α-diethyl-2-hydroxymethyl-3-acetaminobenzylalcohol

To a mixture of 9.5 g of metallic magnesium and 60 ml of diethyl ether was slowly added with stirring a solution of 43 g of ethyl bromide in 120 ml of diethyl ether. The mixed solution was heated for 15 minutes under refluxing and left to stand for cooling. The solution of ethylmagnesium bromide thus prepared above in ether was slowly added with stirring at inner temperature of below 10° C. to a solution of 7.5 g of 4-acetaminophthalide in 120 ml of tetrahydrofuran, followed by stirring at room temperature overnight. After the reaction was over, the reaction mixture was poured into aqueous ammonium chloride solution (saturated) under ice cooling and extracted twice with 400 ml of ethyl acetate. The combined extracts were concentrated to obtain an oily substance. The oily substance was purified by silica gel column chromatography to obtain 8.0 g of α,α-diethyl-2-hydroxymethyl-3-acetaminobenzyl alcohol in the colorness oily substance.

$^1$H-NMR (CDCl$_3$) δppm 1.6 (6H, t, J=6.0 Hz), 2.1 (3H, s), 3.6 (2H, br. s), 5.0 (2H, s), 7.2–7.8 (3H, m), 8.7 (1H, br. s).

Synthesis Example 3

Synthesis of 3,3-diethyl-7-acetaminophthalide

To a solution of 8.0 g of α,α-diethyl-2-hydroxymethyl-3-acetaminobenzyl alcohol in 300 ml of tetrahydrofuran was added 32 g of activated manganese dioxide and the mixture was allowed to react for 6 hours under refluxing. After the reaction was over, the reaction mixture was left to stand for cooling and filtered on a glass filter having a bed of celite. The residue was washed with 100 ml of tetrahydrofuran. The filtrate and the washed solution were combined and concentrated to obtain an oily substance. The oily substance was purified by silica gel column chromatography to obtain 4.9 g of 3,3-diethyl-7-acetaminophthalide in the colorless oily substance.

$n_D^{23.5}$ 1.5376.

$^1$H-NMR (CDCl$_3$) δ ppm 0.75 (6H, t, J=6.0 Hz), 1.8–2.3 (4H, m), 2.3 (3H, s), 7.0 (1H, d, J=8.0 Hz), 7.6 (1H, t, J=8.0 Hz), 8.5 (1H, d, J=8.0 Hz), 9.7 (1H, br. s)

Synthesis Example 4

Synthesis of 1,1-diethyl-3-methyl-3-hydroxy-2-oxa-4-acetaminoindan

To a solution of 4.9 g of 3,3-diethyl-7acetaminophthalide in 80 ml of tetrahydrofuran was slowly added dropwise 43 ml of a solution of methyllithium in ether (1.4M) at −20° C., followed by stirring at the same temperature for 20 minutes. After the reaction was over, the reaction mixture was poured into aqueous ammonium chloride solution (saturated) under ice cooling and extracted twice with 200 ml of ethyl acetate. The combined extracts were concentrated to obtain 5.3 g of 1,1-diethyl-3-methyl-3-hydroxy-2-oxa-4-acetaminoindan as an oily substance.

$^1$H-NMR (CDCl$_3$) δ ppm 0.75 (3H, t, J=6.0 Hz), 0.8 (3H, t, J=6.0 Hz), 1.8 (3H, s), 1.4–2.1 (4H, m), 2.15 (3H, s), 4.5 (1H, br. s), 6.8 (1H, d, J=8.0 Hz), 7.3 (1H, t, J=8.0 Hz), 7.95 (1H, d, J=8.0 Hz), 8.0 (1H, s).

Synthesis Example 5

Synthesis of 1,1-diethyl-3-methyl-2-oxa-4-acetaminoindan

To a solution of 5.3 g of 1,1-diethyl-3-methyl-3-hydroxy-2-oxa-4-acetaminoindan in 120 ml of ethanol was added catalytic amounts of conc. hydrochloric acid and palladium carbon, and vigorously stirred for 6 hours at room temperature under a hydrogen atmosphere. After the reaction was over, the reaction mixture was filtered on a glass filter having a bed of celite and the residue was washed with 60 ml of ethyl acetate. The filtrate and the washed solution were combined and concentrated to obtain 4.8 g of 1,1-diethyl-3-methyl-2-oxa-4-acetaminoindan in the oily substance form.

$^1$H-NMR (CDCl$_3$) δ ppm 0.7 (3H, t, J=6.0 Hz), 0.8 (3H, t, J=6.0 Hz, 1.5 (3H, d, J=6.0 Hz), 1.3–2.0 (4H, m), 2.1 (3H, s), 5.4 (1H, q, J=6.0 Hz), 6.7–7.4 (3H, m), 8.1 (1H, s).

Synthesis example 6

Synthesis of 1,1-diethyl-3-methyl-2-oxa-4-aminoindan

To a solution of 4.8 g of 1,1-diethyl-3-methyl-2-oxa-4-acetaminoindan in 60 ml of ethylene glycol and 30 ml of water was added 11 g of potassium hydroxide and the mixture was heated under refluxing for 8 hours under a nitrogen atmosphere. After the reaction was over, the reaction mixture was left to stand for cooling, diluted with 60 ml of water and extracted with 60 ml of chloroform four times. The combined extracts were washed with water three times, and concentrated. The oily substance obtained was purified by silica gel thin layer chromatography to obtain 2.3 g of 1,1-diethyl-3-methyl-2-oxa-4-aminoindan in the colorless oily substance.

$n_D^{22.5}$ 1.5334.

$^1$H-NMR (CDCl$_3$) δ ppm 0.7 (3H, t, J=6.0 Hz), 0.8 (3H, t, J=6.0 Hz), 1.55 (3H, d, J=6.0 Hz), 1.5–2.1 (4H, m), 3.5 (2H br. s), 5.35 (1H, q, J=6.0 Hz), 6.3–6.7 (2H, m), 7.1 (1H, dd, each J=6.0 Hz).

The following are synthesis examples of substituted 4-amino-2-oxaindan derivative having the formula (V).

Synthesis Example 7

The mixture of 6.0 g of 3-acetaminophthalide anhydride and 6.0 g of malonic acid in 5 ml of pyridine was heated with stirring at 90°–100° C. for 3 hours. After the reaction was over, the reaction mixture was poured into dil. hydrochloric acid under ice cooling and extracted with ethyl acetate. The obtained extracts were concentrated. To the residue was added water to obtain crystal form. The crystal was filtered and dried to obtain 5.5 g of 2-acetyl-6-acetaminobenzoic acid.

Yield 85%, mp 130.8° C.

$^1$H-NMR (CDCl$_3$) δ ppm 1.85 (3H, s), 2.16 (3H, s), 4.3–5.1 (1H, br. s), 7.20 (1H, d, J=7.8 Hz), 7.55 (1H, dd, J=7.8, 8.0 Hz), 8.17 (1H, d, J=8.0 Hz), 9.2–9.6 (1H, br. s).

Synthesis Example 8

The mixture of 4.0 g of 2-acetyl-6-acetaminobenzoic acid, 3.1 g of diethyl sulfate and 2.8 g of potassium carbonate in 40 ml of acetone was allowed to react under stirring under refluxing for 5 hours. After the reaction was over, the reaction mixture was poured into ice water and extracted with ethyl acetate. The extract was washed with water and concentrated to obtain 4.1 g of ethyl 2-acetyl-6-acetaminobenzoate.

Yield 91%, mp 88.0° C.

$^1$H-NMR (CDCl$_3$) δ ppm 1.34 (3H, t, J=7.0 Hz), 2.20 (3H, s), 2.50 (3H, s), 4.32 (2H, q, J=7.0 Hz), 7.07 (1H, d, J=7.0 Hz), 7.46 (1H, dd, J+7.0, 8.0 Hz), 8.50 (1H, d, J=8.0 Hz), 9.6–10.1 (1H, br. s).

Synthesis Example 9

To a solution of 0.71 g of ethyl 2-acetyl-6-acetaminobenzoate in 20 ml of tetrahydrofuran was added dropwise 15 ml of a solution of 13.4 mmol of ethyl magnesium bromide below 5° C., followed by stirring at room temperature overnight. The reaction mixture was poured into aqueous ammonium chloride and extracted with ethyl acetate. The obtained extract was concentrated. To the residue dissolved in ethanol was added catalytic amounts of conc. hydrochloric acid and palladium carbon under a hydrogen atmosphere. After the reaction was over, the palladium carbon was removed by filtration and the filtrate was concentrated. The residue was purified by silica gel thin layer chromatography (solvent system; n-hexane: ethyl acetate=1:1 v/v) to obtain 0.20 g of 1,3-diethyl-1-methyl-2-oxa-4-acetaminoindan.

Yield 30%.

$^1$H-NMR (CDCl$_3$) δ ppm 0.6–1.3 (6H, m), 1.34 (3H, s), 1.3–2.1 (4H, m), 2.02 (3H, s), 5.1–5.5 (1H, m), 6.7–7.5 (3H, m), 7.8–8.4 (1H, br. s).

Synthesis Example 10

To a solution of 1.5 g of 1,3-diethyl-1-methyl-2-oxa-4-acetaminoindan in 2 ml of water and 6 ml of ethylene glycol was added 1.7 g of potassium hydroxide and the mixture was heated under refluxing for 8 hours. After the reaction was over, the reaction mixture was poured into water and extracted with ethyl acetate. The extract was concentrated. The residue was purified by silica gel thin layer chromatography (solvent system; n-hexane : ethyl acetate=1:1 v/v) to obtain 0.83 g of 1,3-diethyl-1-methyl-2-oxa-4-aminoindan.

Yield 67%, n$_D^{22.5}$ 1.549.

$^1$H-NMR (CDCl$_3$) δ ppm 1.42 (3H, t, J=6.4 Hz), 1.54 (3H, t, J=7.0 Hz), 1.38, 1.49 (total 3H, each s), 1.3–2.2 (4H, m), 3.3–3.8 (2H, br. s), 5.0–5.4 (1H, m), 6.46 (1H, d, J=7.0 Hz), 6.49 (1H, d, J=7.4 Hz), 7.56 (1H, dd, J=7.0, 7.4 Hz).

The following compounds were produced by the methods.

1,3-Dimethyl-1-ethyl-2-oxa-4-aminoindan   n$_D^{22.5}$ 1.5293.

$^1$H-NMR (CDCl$_3$) δ ppm 0.83 (3H, t, J=7.6 Hz), 1.36, 1.47 (total 3H, each s), 1.52 (3H, d, J=6.0 Hz), 1.4–2.1 (2H, m), 3.2–4.0 (2H, br. s), 5.27 (1H, q, J=6.0 Hz), 6.43 (1H, d, J=8.0 Hz), 6.48 (1H, d, J=8.0 Hz), 7.04 (1H, dd, each 8.0 Hz).

1,3-Dimethyl-1-n-propyl-2-oxa-4-aminoindan   n$_D^{23.0}$ 1.5335.

$^1$H-NMR (CDCl$_3$) δ ppm 0.5–1.1 (3H, br. t), 1.37, 1.48 (total 3H, each s), 1.53 (3H, d, J=6.2 Hz), 1.3–2.0 (4H, m), 3.1–3.8 (2H, br. s), 5.27 (1H, q, J=6.2 Hz), 6.45 (1H, d, J=8.0 Hz), 6.50 (1H, d, J=8.0 Hz), 7.06 (1H, dd, J=8.0, 8.0 Hz).

1,3-Diethyl-1-methyl-2-oxa-4-aminoindan   n$_D^{22.5}$ 1.5459.

$^1$H-NMR (CDCl$_3$) δ ppm 1.42 (3H, t, J=6.4 Hz), 1.54 (3H, t, J=7.0 Hz), 1.38, 1.49 (total 3H, each s), 1.3–2.2 (4H, m), 3.3–3.8 (2H, br. s), 5.0–5.4 (1H, m), 6.46 (1H, d, J=7.0 Hz), 6.49 (1H, d, J=7.4Hz), 7.56 (1H, dd J=7.0, 7.4 Hz).

The following are synthesis examples of substituted 4-amino-2-oxaindan derivative having the formula (VI).

Synthesis Example 11

To a solution of 1.4 g of ethyl 2-acetyl-6-acetoaminobenzoate in 10 ml of ethanol and 2 ml water was slowly added 0.72 g of sodium borohydride at 0° C. After being stirred at room temperature for a hour, the reaction mixture was poured into 5% aqueous hydrochloric acid, left to stand at room temperature for a hour and then extracted with ethyl acetate. The extract was concentrated. The residue was purified by silica gel thin layer chromatography to obtain 0.80 g of 3-methyl-7-acetaminophthalide in the white crystal form.

mp 112.1° C.

$^1$H-NMR (CDCl$_3$) δppm 1.65 (3H, d, J=6.0 Hz), 2.25 (3H, s), 5.5 (1H, q, J=6.0 Hz), 6.95 (1H, d, J=6.0 Hz), 7.55 (1H, t, J=6.0 Hz), 8.4 (1H, d, J=6.0 Hz), 9.5 (1H, br. s).

Synthesis Example 12

To a solution of 0.8 g of 3-methyl-7-acetaminophthalide in 10 ml of tetrahydrofuran was added dropwise 9.8 ml of a solution of methyllithium in ether (1.19M) at −20° C., followed by stirring at the same temperature for 30 minutes. After the reaction was over, the reaction mixture was poured into aqueous ammonium chloride solution and extracted with ethyl acetate. The obtained extract was concentrated and then to the residue dissolved in ethanol was added catalylic amounts of hydrochloric acid and palladium carbon under a hydrogen atmosphere. After the reaction was over, the palladium carbon was removed by filtration and the filtrate was concentrated. The residue was purified by silica gel thin layer chromatography (solvent system; n-hexane: ethyl acetate=1:1 v/v) to obtain 0.72 g of 1,3-dimethyl-2-oxa-4-acetaminoindan.

Yield 90% mp 184.1° C.

$^1$H-NMR (CDCl$_3$) δ ppm 1.45 (3H, d, J=6.0 Hz), 1.5 (3H, d, J=6.0 Hz), 2.1 (3H, s), 5.0–5.6 (2H, m), 6.8–7.9 (4H, m).

Synthesis Example 13

To a solution of 0.7 g of 1,3-dimethyl-2-oxa-4-acetoaminoindan in 2 ml of water and 6 ml of ethylene glycol was added 1.9 g of potassium hydroxide and the mixture was heated under refluxing for 8 hours. After the reaction was over, the reaction mixture was poured into water and extracted with ethyl acetate. The extract was concentrated. The residue was purified by silica gel thin layer chromatography to obtain 0.45 g of 1,3-dimethyl-2-oxa-4-aminoindan.

Yield 84%, mp 94.1° C.

$^1$H-NMR (CDCl$_3$) δ ppm 1.5 (3H, d, J=6.0 Hz), 1.55 (3H, d, J=6.0 Hz), 3.6 (2H, br. s), 5.0–5.5 (2H, m), 6.55 (2H, br. d, J=8.0 Hz), 7.1 (1H, br. t, J=8.0 Hz).

The following compounds was produced by the same methods.

1-Ethyl-3-methyl-2-oxa-4-aminoindan
mp 54.1° C.

$^1$H-NMR 1.0(3H, d, J=6.0 Hz), 1.55 (3H, d, J=6.0 Hz), 1.3–2.0 (2H, m), 3.6 (2H, br. s), 4.8–5.4 (2H, m), 6.55 (2H, br. d, J=8.0 Hz), 7.1 (1H, br. t, J=8.0 Hz).

The following are formulation examples where the present compounds used are indicated by the numbers given in Table 1 and Synthesis examples are parts by weight.

Formulation Example 1

Fifty parts of each of the present compounds (1)–(9), 3 parts of calcium lignosulfonate, 2 parts of sodium lauryl sulfate and 45 parts of synthetic hydrated silicon dioxide are thoroughly pulverized and mixed to obtain a wettable powder containing an active ingredient concentration of 50%.

Formulation Example 2

Ten parts of each of the present compounds (1)–(9), 14 parts of polyoxyethylenestyrylphenyl ehter, 6 parts of calcium dodecylbenzenesulfonate and 70 parts of xylene are thoroughly mixed to obtain an emulsifiable concentrate containing an active ingredient concentration of 10%.

Formulation Example 3

Two parts of each of the present compounds (1)–(9), 1 part of synthetic hydrated silicon dioxide, 2 parts of calcium lignosulfonate, 30 parts of bentonite and 65 parts of kaolin clay are thoroughly pulverized and mixed, well kneaded with water, then granulated and dried to obtain a granule containing an active ingredient concentration of 2%.

Formulation Example 4

Twenty five parts of each of the present compounds (1)–(9), 3 parts of polyoxyethylene sorbitan monooleate, 3 parts of CMC and 69 parts of water are mixed and wet-pulverized to particle size of not more than 5 microns to obtain a suspension formulation containing an active ingredient concentration of 25%.

Formulation Example 5

Two parts of each of the present compounds (1)–(9), 88 parts of kaolin clay and 10 parts of talc are thoroughly pulverized and mixed to obtain a dust containing an active ingredient concentration of 2%.

Formulation Example 6

Ten parts of each of the present compounds (1)–(9), 1 part of polyoxyethylenestyrylphenylether and 89 parts of water are mixed to obtain a liquid containing an active ingredient concentration of 10%.

The effect of the present compounds as an active ingredient of fungicides will be shown by the following test examples. The present compounds used are indicated by the compound number given in Table 2 and Synthesis Examples and the compounds used for comparison are indicated by the compounds given in Table 3.

TABLE 3

| Compounds | Chemical formula | Note |
|---|---|---|
| A | (structure: two phenyl rings connected by C(=O)-NH group; left ring has CH$_3$ substituent, right ring has OC$_3$H$_7$(i) substituent) | Commercially available fungicide (mepronil) |

The controlling effect is determined by observing with the naked eye the condition of disease of test plants on examination, namely, the degree of fungus colony and infected area of leaf and stem and grading the condition of diseases into the following six indices 0, 1, 2, 3, 4 and 5:

The above grading is applied to all of the following test examples.

Test example 1

Test for preventive controlling effect on sheath blight (*Rhizoctonia solani*) of rice Sandy loam was filled in a plastic pot and rice (var.: Kinki No. 33) was sowed and cultivated in a greenhouse for 20 days to grow to seedlings in the 4-5 leaf stages. The test compounds were formulated into emulsifiable concentrates in accordance with the Formulation Example 2 and they were diluted with water to a given concentration. These were foliar-sprayed onto the seedlings to allow them to thoroughly deposit on the leaf surface. After 4 hours from the spraying, the seedlings were inoculated with agar piece containing *Rhizoctonia solani*. After inoculation, the seedlings were grown at 28° C. for 4 days under highly humid condition and the controlling effects were observed. The results are shown in Table 4.

TABLE 4

| Test compounds | Concentration of active ingredient (ppm) | Controlling effect |
|---|---|---|
| (1) | 50 | 5 |
| | 25 | 5 |
| (2) | 50 | 5 |
| | 25 | 5 |
| (3) | 50 | 5 |
| | 25 | 5 |
| (6) | 50 | 5 |
| | 25 | 5 |
| (7) | 50 | 5 |
| | 25 | 5 |
| (8) | 50 | 5 |
| | 25 | 5 |
| A | 50 | 3 |
| | 25 | 0 |

Text Example 2

Test for systemic controlling effect on sheath blight (*Rhizoctonia solani*) of rice Sandy loam was filled in a 130 ml plastic pot and rice (var.: Kinki No. 33) was sowed and cultivated in a greenhouse for 3 weeks to grow to seedlings in the 4-5 leaf stages. The test compounds formulated into wettable powders in accordance with Formulation Example 1 and they were diluted with water and drenched in a given amount to the soil. After drench, the seedlings were grown in a greenhouse for 7 days and inoculated with agar piece containing *Rhizoctonia solani*. After inoculation, the seedlings were grown at 28° C. for 4 days under a highly humid condition and the controlling effect was observed. The results are shown in Table 5.

TABLE 5

| Test compounds | Dosage of active ingredient (g/10a) | Controlling effect |
| --- | --- | --- |
| (1) | 100 | 4 |
| (2) | 100 | 5 |
| (3) | 100 | 5 |
| (6) | 100 | 5 |
| (7) | 100 | 4 |
| (8) | 100 | 4 |
| A | 100 | 0 |

Test Example 3

Test for controlling effect on southern blight (*Corticium rolfsii*) of kidney bean Sandy loam well mixed with *Corticium rolfsii* which was previously cultured in bran medium was filled in a 250 ml plastic pot and kidney beam (var.: Taishokintoki) was sowed. The test compounds were formulated into wettable powders in accordance with Formulation Example 1 and diluted with water. A given amount of the test compound was drenched into the soil. After the drench, cultivation was made for 3 weeks in a greenhouse and controlling effect was examined by observing the degree of disease of the stem in the vicinity of the soil surface. The results are shown in Table 6.

TABLE 6

| Test compounds | Dosage of active ingredient (g/10a) | Controlling effect |
| --- | --- | --- |
| (2) | 200 | 5 |
| (3) | 200 | 5 |
| (6) | 200 | 5 |
| A | 500 | 3 |

Test Example 4

Test for curative controlling effect on brown rust (*Puccinia recondita*) of wheat Sandy loam was filled in a plastic pot and wheat (var.: Norin No. 73) was sowed and grown in a greenhouse for 10 days to seedlings of the 2-3 leaf stages, which were inoculated with spores of *Puccinia recondita*. After inoculation, the seedlings were grown at 23° C. for one day under a highly humid condition and onto these seedlings was foliar-sprayed the test compound formulated into emulsifiable concentrate in accordance with Formulation Example 2 and diluted with water to a given concentration, so that the compound was thoroughly deposited on the leaf surface. After spraying, the seedlings were cultivated at 23° C. for 7 days under illumination and the controlling effect was observed. The results are shown in Table 7.

TABLE 7

| Test Compounds | Concentration of active ingredient (ppm) | Controlling effect |
| --- | --- | --- |
| (2) | 500 | 5 |
| (3) | 500 | 5 |
| (6) | 500 | 5 |

We claim:

1. A substituted pyrazole carboxylic acid derivative having the formula:

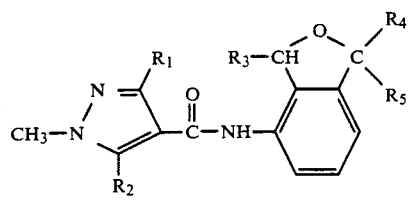

wherein $R_1$ is a methyl or trifluoromethyl group; $R_2$ is a halogen atom; $R_3$ and $R_4$ are, same or different, a methyl or ethyl group; $R_5$ is an ethyl, propyl, butyl group or hydrogen atom.

2. The compound according to claim 1, wherein $R_1$ is a methyl or trifluoromethyl group; $R_2$ is a chlorine atom; $R_3$ and $R_4$ are, same or different, a methyl or ethyl group; $R_5$ is an ethyl, n-propyl, n-butyl group or hydrogen atom.

3. The compound according to claim 1, wherein $R_1$ is a methyl group; $R_2$ is a chlorine atom; $R_3$ and $R_4$ are a methyl group; $R_5$ is an ethyl group.

4. The compound according to claim 1, wherein $R_1$ is a methyl group; $R_2$ is a chlorine atom; $R_3$ and $R_4$ are a methyl group; $R_5$ is a n-propyl group.

5. An agricultural or horticultural fungicide which contains, as an active ingredient, a substituted pyrazole carboxylic acid derivative having the formula:

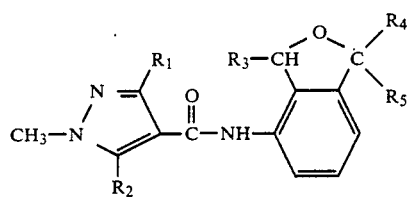

where $R_1$ is a methyl or trifluoromethyl group; $R_2$ is a halogen atom; $R_3$ and $R_4$ are, same or different, a methyl or ethyl group; $R_5$ is an ethyl, propyl, butyl group or hydrogen atom, with an inert carrier.

6. A method for controlling fungi which comprises applying a fungicidally effective amount of a substituted pyrazole carboxylic acid derivative having the formula:

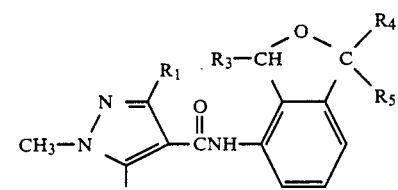

wherein $R_1$ is a methyl or trifluoromethyl group; $R_2$ is a halogen atom; $R_3$ and $R_4$ are, same or different, a methyl or ethyl group; $R_5$ is an ethyl, propyl, butyl group or hydrogen atom.

7. The method according to claim 5 wherein the fungi are plant pathogenic fungi.

* * * * *

UNITED STATES PATENT AND TRADEMARK OFFICE
CERTIFICATE OF CORRECTION

PATENT NO. : 5,049,575
DATED : September 17, 1991
INVENTOR(S) : Tadashi OHSUMI ET AL It is certified that error appears in the above-identified patent and that said Letters Patent is hereby corrected as shown below:

On the Title page

Change name of Assignee:

from "Sumitomo Chemical Company"

to --Sumitomo Chemical Company, Limited--

Signed and Sealed this

Twenty-third Day of February, 1993

Attest:

STEPHEN G. KUNIN

Attesting Officer

Acting Commissioner of Patents and Trademarks